United States Patent
Ogawa et al.

(10) Patent No.: US 7,403,287 B2
(45) Date of Patent: Jul. 22, 2008

(54) SENSING ELEMENT USED IN SENSING DEVICE FOR SENSING TARGET SUBSTANCE IN SPECIMEN BY USING PLASMON RESONANCE

(75) Inventors: Miki Ogawa, Tokyo (JP); Norihiko Utsunomiya, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 154 days.

(21) Appl. No.: 11/448,070

(22) Filed: Jun. 7, 2006

(65) Prior Publication Data

US 2006/0279738 A1    Dec. 14, 2006

(30) Foreign Application Priority Data

Jun. 8, 2005    (JP)    ............................ 2005-168708

(51) Int. Cl.
*G01N 21/55*    (2006.01)
(52) U.S. Cl. ................................ 356/445
(58) Field of Classification Search .......... 356/445–448
See application file for complete search history.

(56) References Cited

U.S. PATENT DOCUMENTS

| | | | | |
|---|---|---|---|---|
| 4,448,485 | A * | 5/1984 | Bergman et al. ............ 359/328 |
| 5,327,225 | A * | 7/1994 | Bender et al. .............. 356/445 |
| 5,618,760 | A * | 4/1997 | Soh et al. ................... 438/703 |
| 6,022,810 | A * | 2/2000 | Kusumi et al. ............. 438/738 |
| 6,048,623 | A * | 4/2000 | Everhart et al. ............ 428/464 |
| 6,194,323 | B1 * | 2/2001 | Downey et al. ............. 438/717 |
| 6,424,418 | B2 * | 7/2002 | Kawabata et al. .......... 356/445 |
| 6,534,798 | B1 * | 3/2003 | Scherer et al. ............... 257/98 |
| 6,682,988 | B1 * | 1/2004 | Babcock .................... 438/443 |
| 6,699,719 | B2 * | 3/2004 | Yamazaki et al. ............ 506/30 |
| 6,782,179 | B2 * | 8/2004 | Bozhevolnyi et al. ....... 385/131 |
| 6,795,192 | B2 * | 9/2004 | Dickopf et al. ............. 356/445 |
| 6,807,323 | B2 * | 10/2004 | Beom et al. .................. 385/12 |
| 6,982,819 | B2 * | 1/2006 | Sawin et al. ................ 359/245 |
| 7,057,786 | B2 * | 6/2006 | Sawin et al. ................ 359/245 |
| 7,079,250 | B2 * | 7/2006 | Mukai ........................ 356/445 |
| 7,292,334 | B1 * | 11/2007 | Bratkovski et al. ......... 356/301 |
| 2002/0044893 | A1 * | 4/2002 | Corn et al. ................. 422/68.1 |
| 2002/0088970 | A1 * | 7/2002 | Yu et al. ...................... 257/12 |
| 2004/0009516 | A1 * | 1/2004 | Nelson et al. .................. 435/6 |
| 2005/0062973 | A1 * | 3/2005 | Kim et al. .................. 356/445 |

FOREIGN PATENT DOCUMENTS

| | | |
|---|---|---|
| JP | 2000-356587 | 12/2000 |
| JP | 2003-268592 | 9/2003 |
| JP | 2004-191341 | 7/2004 |

* cited by examiner

*Primary Examiner*—L. G. Lauchman
*Assistant Examiner*—Jarreas C Underwood
(74) *Attorney, Agent, or Firm*—Fitzpatrick, Cella, Harper & Scinto

(57) ABSTRACT

A method of producing a sensing element used in a detecting device for detecting a target substance in a specimen with the use of plasmon resonance. The method includes the steps of forming an insulating layer on a substrate, the surface of the substrate having an electroconductive layer including a first electroconductive material, forming a plurality of holes through the insulating layer to form an insulating pattern, filling up the holes with a second electroconductive material to form a metallic pattern, removing the insulating pattern, and removing a region other than the region sandwiched by the metallic pattern and the substrate in the electroconductive layer, using the metallic pattern as a mask.

5 Claims, 11 Drawing Sheets

SENSING ELEMENT USED IN SENSING DEVICE FOR SENSING TARGET SUBSTANCE IN SPECIMEN BY USING PLASMON RESONANCE

This application claims priority from Japanese Patent Application No. 2005-168708, filed Jun. 8, 2005, which is hereby incorporated by reference herein.

BACKGROUND OF THE INVENTION

1. Field of the Invention

The present invention relates to a sensing element and a detecting device by using plasmon resonance, and a method for producing the sensing element. The present invention relates to a so-called biosensor with the use of a recognition capability peculiar to a substance of a biometric origin or a substance similar thereto.

2. Related Background Art

A biosensor is a measuring device making use of the excellent molecular recognition capability of living matter and a biomolecule. The living matter has a combination of substances having a mutual affinity with each other, such as an enzyme-substrate, an antigen-body and DNA-DNA. The biosensor makes use of a principle that one substance of the combination, which is immobilized or carried on a substrate, can selectively measure the other substance. In recent years, the biosensor has been expected to be widely applied not only to the medical field, but also, to fields of environment and food, so that a biosensor, which is installable everywhere or is transportable, is small and lightweight, has been expected, to be used in wider application areas.

Currently, as one of highly sensitive sensing systems, a sensor, using an interaction between plasmon existing on a metal surface and metallic microparticles and light, has been diligently studied.

A conventional sensor using surface plasmon resonance (SPR sensor) uses a phenomenon that when light is launched onto the surface of a metallic thin film, only light incident from a certain particular angle resonates with and is absorbed by plasmon on the metal surface, and the reflected light is attenuated. The angle at which the absorption occurs is sensitive to a surface condition (refractive index) of the metallic thin film, so that the sensor can measure a reaction (for instance, an antigen-antibody reaction) occurring on the metal surface by measuring the intensity of reflected light while changing the incidence angle.

However, the SPR sensor has had a problem of needing a prism from a structural standpoint, and consequently, making an optical system complicated. The SPR sensor also had a problem that it cannot be applied to a substrate with a curved surface, because of the need to prepare a metallic thin film by vacuum deposition, which limited the substrate and a device structure. Because of these problems, the SPR was considered to be difficult to miniaturize.

In such a background, Japanese Patent Application Laid-Open No. 2000-356587 proposed a sensor using localized surface plasmon resonance (an LSPR sensor) in metallic microparticles. The localized plasmon resonance sensor detects the refractive index of a medium around the metallic microparticles, by measuring an absorbance of light having been transmitted through the metallic microparticles, which are fixed like a membrane on a substrate surface.

Furthermore, Japanese Patent Application Laid-Open No. 2003-268592 discloses an invention of forming mutually isolated metallic particles in a plurality of pores in anodized alumina oxide for the purpose of regularly and independently arranging the metallic particles in an arbitrary uniform size and an arbitrary array, and using it for a plasmon resonance device.

Furthermore, Japanese Patent Application Laid-Open No. 2004-191341 discloses a molecule-recognizing element applicable to the biosensor, which is prepared by introducing a metallic material in columnar pores in a porous film formed on the substrate, preparing a columnar structure by removing the porous film and immobilizing a molecule-recognizing material on it. The above Japanese patent document also discloses that the metallic material may be introduced through electrodeposition (electrolysis plating).

SUMMARY OF THE INVENTION

According to an aspect of the present invention, there is provided a sensing element used in a sensing device for detecting a target substance in a specimen with the use of plasmon resonance, the sensing element comprising:

a substrate, an electroconductive layer provided on a substrate of the surface, and a layer comprised of a metallic pattern connected to the electroconductive layer, wherein the metallic pattern is exposed at the surface of the layer comprised of the metallic pattern, and a periodic unit of the metallic pattern has a size in a range of 50 nm to 450 nm.

The layer comprised of the metallic pattern is preferably comprised of gold or silver.

The layer comprised of the metallic pattern is preferably comprised of two or more layers of different materials.

The metallic pattern is preferably comprised of metallic dots. The metallic dots are preferably comprised of gold or silver. The metallic dots are comprised of two or more layers of different materials.

Alternatively, the metallic pattern is comprised of holes formed in the layer comprised of the metallic pattern.

The electroconductive layer is preferably optically transparent.

A distance between the adjacent periodic units of the metallic pattern is preferably in a range of 50 nm to 2000 nm.

The surface of the metallic pattern preferably has a capturing body for capturing the target substance.

According to another aspect of the present invention, there is provided a detecting device for detecting a target substance in a specimen with the use of plasmon resonance, the detecting device comprising:

the above sensing element, a light source for irradiating the sensing element with light, and a light-receiving element for detecting the light reflected from or transmitted through the sensing element.

According to still another aspect of the present invention, there is provided a sensing element used in a detecting device for detecting a target substance in a specimen with the use of plasmon resonance, comprising:

a substrate, an electroconductive layer provided on a surface of the substrate, and a metallic film which is connected to the electroconductive layer and has a plurality of openings with a size in a range of 50 nm to 450 nm, wherein the metallic film is exposed at the surface of the sensing element.

According to a further aspect of the present invention, there is provided a method of producing a sensing element used in a detecting device for detecting a target substance in a specimen with the use of plasmon resonance, the method comprising the steps of:

preparing a substrate having an electroconductive layer, forming an insulating layer on the electroconductive layer, selectively removing the insulating layer to make the electroconductive layer appear, and depositing a metal on the appearing electroconductive layer with an electrolytic plating method.

DETAILED DESCRIPTION OF THE PREFERRED EMBODIMENTS

A method of preparing a sensing element according to the present invention is a method of preparing a sensing element used in a sensing device for sensing a target substance in a specimen with the use of plasmon resonance, and includes the steps of preparing a substrate having an electroconductive layer, forming an insulating layer on the electroconductive layer, selectively removing the insulating layer to make the electroconductive layer appear, and depositing a metal on the appearing electroconductive layer with an electrolytic plating method. The method makes the electroconductive layer appear by selectively removing the insulating layer, and deposits the metal capable of inducing plasmon resonance with the electrolytic plating method. Owing to these steps, the method can deposit the metal with a desired shape at a desired spacing. The method can control the change of the shape and size of metallic dots, which may be caused by removing a resist layer located under a metallic layer, when patterning the metal with a lift-off technology to form the metallic dots. The method also can form the metallic dots comparatively easily by using the plating method, though it is difficult to control a condition when forming the metallic dots by etching a chemically extremely-stable metallic layer, such as gold.

On the other hand, a sensing element according to the present invention can highly sensitively detect objective substances, because the metallic dots or openings in a metallic layer are controlled to have a specified size.

A sensing element according to the present invention is an element for detecting a target substance in a specimen with the use of plasmon resonance, and has a structure in which a metallic pattern is placed so as to contact with an electroconductive layer provided on a substrate. A detecting device for the target substance can be formed by combining the sensing element, with a light source for illumination and a light-receiving element. In the next place, the sensing element and the detecting device using it according to the present invention will be described in detail.

A sensing element according to the present invention is a sensing element for sensing a target substance in a specimen by using a plasmon resource method, and includes the element that has a substrate having a metallic pattern formed thereon so as to be connected with an electroconductive layer on the substrate.

(Metallic Pattern)

A metallic pattern according to the present invention is a metallic structure for causing a plasmon resource phenomenon, which has a pattern formed of dots or holes as a metallic layer to improve detection sensitivity as a sensing element. The metallic pattern according to the present invention will be described by taking a pattern formed of the metallic dots (hereafter referred to as a "dot pattern") as an example.

Figure 1A:
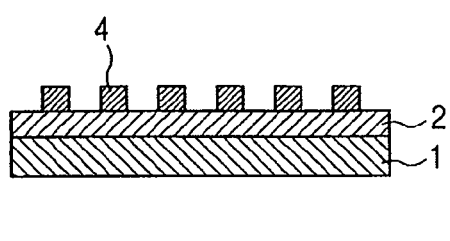
FIGS. 1A, 1B, 1C, 1D and 1E are schematic block diagrams showing examples of metallic dots and an electroconductive layer formed on a substrate, according to the present invention.
Figure 1B:
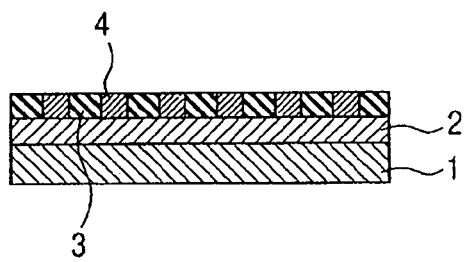
Figure 4A:
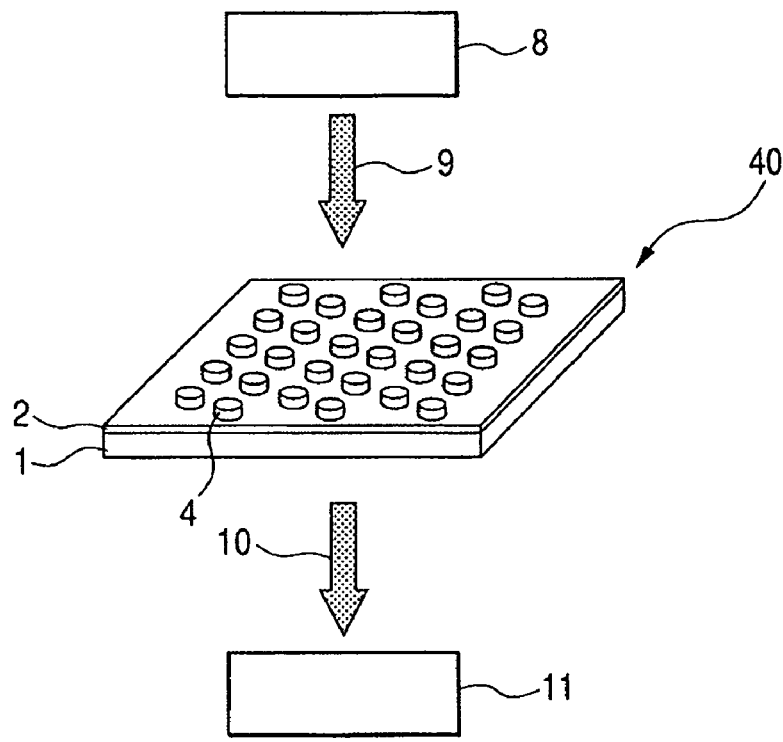
FIGS. 4A and 4B are views showing examples of a sensing device according to Examples 1 and 2.
Figure 4B:
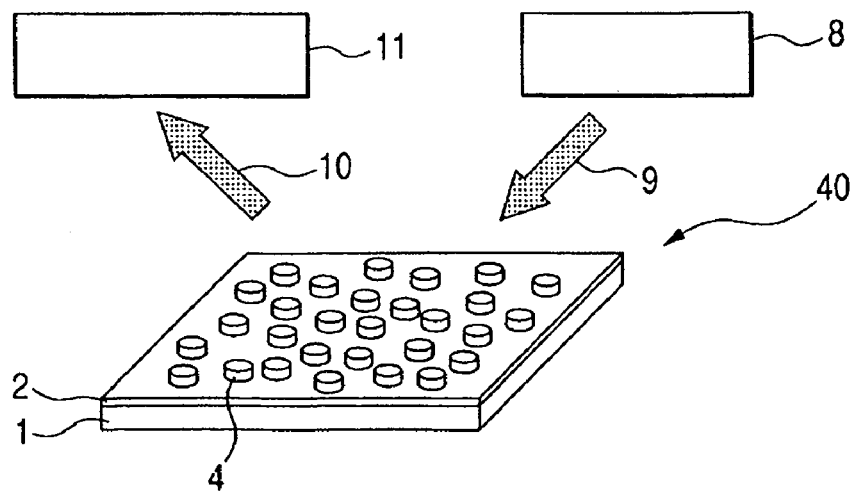

A dot pattern according to the present invention is formed of a dot-shaped metal 4 (hereafter referred to as a metallic dot), which is connected to an electroconductive layer 2 placed on the surface of a substrate 1 or is integrated with the electroconductive layer, as is shown in FIGS. 4A and 4B. The metallic dot and the electroconductive layer are electrically conducted. When the electroconductive layer and the metallic dot are integrated, the electroconductive layer and the metallic dot form a continuous solid layer. An example is a structure in which the electroconductive layer and the metallic dot are integrally formed from the same metallic material. A preparation method according to the present invention forms the metallic dot on the electroconductive layer with a method capable of precisely controlling the shape and array, which will be described later, and accordingly, can easily obtain the shape of the metallic dot and the independent array on the electroconductive layer, which are necessary for highly sensitive detection. In addition, there may be such a space between the metallic dots 4 so as to isolate each of the metallic dots, as is shown in FIG. 1A, but alternatively, an insulating layer 3 may be formed between the metallic dots 4 and isolate each of the metallic dots, as is shown in FIG. 1B. In addition, in order to make uniform an interaction between the metallic dots to stabilize the function of an element, it is preferable to arrange the metallic dots so that spacing between the metallic dots can be substantially equal. In the present invention, the size of the metallic dot is preferably controlled to be in a range of 50 nm or larger, but 450 nm or smaller, for the purpose of giving adequate detection sensitivity to the sensing element. Here, the size of the metallic dot means the planar size of the metallic dot; and specifically, means a diameter of a circle when the metallic dot is a circle, a length of one side when the metallic dot is a square, and a length of a long side when the metallic dot is a rectangle. In addition, the spacing between the adjacent metallic dots is preferably controlled to be 50 nm or more, but 2,000 nm or less, for the purpose of giving adequate detection sensitivity to the sensing element. It is considered to be the reason that the plasmon of the metallic dots gives influence to each other through interaction.

Figure 1C:
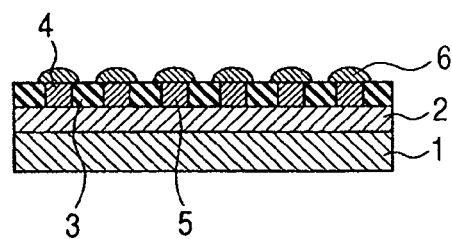
Figure 1D:
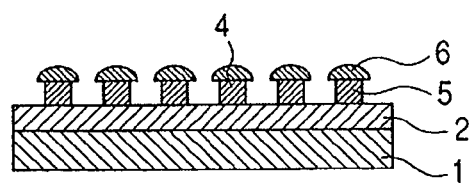
Figure 1E:
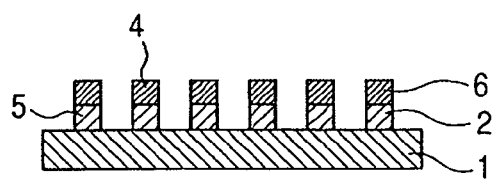

It is essential only that a metallic dot includes a metal capable of causing a plasmon resonance phenomenon, and it is preferable to employ at least one of gold, silver and copper for such a metal. Particularly, silver has a high sensitivity when used in a sensing element, although having a low corrosion resistance, and accordingly, is preferably employed. Gold has a high corrosion resistance, and accordingly, is used for preparing a stable sensing element. Furthermore, the metallic dot is preferably formed of two or more layers made of different materials. For instance, the metallic dot formed of the two layers of the layer made of gold and the layer made of silver can make use of the high sensitivity of silver, while complementing the corrosion resistance of silver, and is thus preferable. In the present invention, as is shown in FIGS. 1C and 1D, the metallic dot formed of the two metallic layers 5 and 6 can be easily prepared. Furthermore, another arrangement of a metallic layer than the one described above and a multilayer structure formed of two or more layers can be employed in the present invention. It is also possible to form the electroconductive layer as one part of the metallic dot, specifically, integrally form the metallic dot so as to include the electroconductive layer, as is shown in FIG. 1E, which is preferable for improving the transparency of a sensing element as well.

Figure 10:
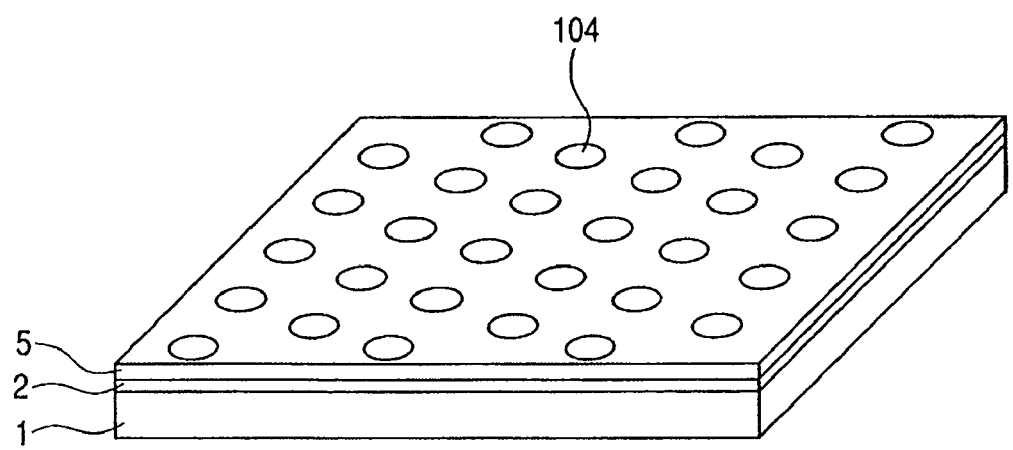
FIG. 10 is a schematic block diagram showing an example of an electroconductive layer and a hole pattern of the metal formed on a substrate, according to the present invention.

A metallic pattern according to the present invention may also be a metallic layer in which holes are formed in the metallic layer, so as to form a pattern (hereafter referred to as a hole pattern). The metallic pattern includes a pattern in which a metallic film 5 having hole-shaped cavities 104 (openings), as is shown in FIG. 10, is formed so as to be connected with the electroconductive layer 2 provided on the surface of a substrate 1. A method according to the present invention can form the above-described hole-shaped cavity on the electroconductive layer with a method capable of precisely controlling the shape and the array, and accordingly, can easily obtain the shape of the hole-shaped cavity and the independent array on the electroconductive layer, which are necessary for highly sensitive detection. In such a hole pattern, a metallic material and a layer structure can be appropriately selected similarly to the case of the metallic dot.

In addition, in the present invention, a dot and a hole are schematically shown in a columnar shape, but the shape is not limited thereto, as long as the shape can give sufficient sensitivity to a sensing element. In the present invention, the size of an opening formed in a metallic film is preferably controlled to be in a range of 50 nm or larger, but 450 nm or smaller, for the purpose of giving adequate detection sensitivity to the sensing element. In addition, the spacing between the adjacent openings is preferably controlled to be 50 nm or more, but 2,000 nm or less, for the purpose of giving adequate detection sensitivity to the sensing element.

(Substrate)

A material and a shape of a substrate are not limited, as long as the substrate can hold a required structure, including a metallic pattern and an electroconductive layer thereon, so that the usable material is general for a substrate and includes a resin. Also, an inorganic material including glass and silicon, a metal, and a metal oxide, can be used. However, when the substrate is used in a detecting device which makes light transmit through a metallic pattern, and further detects the transmitted light through a substrate as "light transmitted through a sensing element", the substrate is preferably made of a transparent material for a wavelength of an incident measuring light (incident light) and the light to be detected, namely, a material having translucency for the light for the detection. The detecting device also can use the light which has transmitted through the metallic pattern and then has been reflected from the sensing element for the detection, and in this case, employs the substrate made of such a material so as to reflect incident light and the light with the wavelength to be detected.

(Electroconductive Layer)

A sensing element according to the present invention has a metallic pattern formed so as to be connected to an electroconductive layer on a substrate. The electroconductive layer may be arranged on the whole area of a substrate surface, or may be arranged on a region having a necessary area at a necessary predetermined position for detection on the substrate surface. In the next place, the electroconductive layer will be described, while taking the metallic pattern formed of a dot pattern as an example, and referring to the drawings. FIG. 1A shows a configuration having the electroconductive layer 2 arranged on the whole area of the substrate 1. Furthermore, the electroconductive layer 2 may be arranged on the substrate 1 so as to individually correspond to each of metallic dots 4, as is shown in FIG. 1E. In addition, it is acceptable to form a plurality of the electroconductive layers separated from each other on the substrate, and respectively form a plurality of the metallic dots on them.

An objective highly-sensitive sensing element in the present invention is prepared by forming a metallic pattern so as to be connected with an electroconductive layer, as will be described later in a preparation method. Accordingly, a structure formed of the electroconductive layer and the metallic pattern is not limited to the above-described structure, as long as the electroconductive layer and the metallic pattern form such a connected structure so as to enable highly sensitive detection. Furthermore, in the present invention, the electroconductive layer may be eventually formed as one part of the metallic pattern. In other words, the electroconductive layer 2 is a metallic layer 5, and may be used as a metallic dot 4 formed of a bilayer together with a metallic layer 6, as is shown in FIG. 1E. As a matter of course, these configurations can be similarly applied to the metallic pattern having other shapes according to the present invention, such as a hole pattern.

A general material, such as a metal and an inorganic oxide, may be used as an electroconductive material used for forming an electroconductive layer. The material for forming the electroconductive layer can be selected from various materials and be used as the material, as long as it can form the electroconductive layer on a substrate and can be adequately plated through an electrolytic method, as will be described later in a preparation method. When the electroconductive layer is formed as one part of the metallic dot as shown in FIG. 1E, the material is selected from those capable of forming the metallic layer 5. However, when the detecting device uses the light which has transmitted through the metallic dot and further has transmitted through the substrate, as the light having transmitted through a sensing element for detection, it is preferable to employ the following material. Specifically, the electroconductive layer is formed as a substantially transparent layer with respect to a wavelength of the incident measurement light (incident light) and light to be detected, in such a range so as to give sufficient detection sensitivity to a sensing element. An electroconductive material capable of forming such a transparent layer (translucent layer) includes, for instance, a metal oxide, such as tin oxide, indium oxide, zinc oxide, titanium oxide, tin-oxide-doped indium oxide (ITO), fluorine-doped tin oxide (FTO) and antimony-doped tin oxide (ATO). A thin film of a metallic material can also be used as an electroconductive layer other than the metal oxide layer. The thin film of the metallic material is slightly inferior in transparency to the metal oxide-based material, but has sufficient transparency to be applied to the sensing element, has high electroconductivity, and accordingly, is preferably employed.

(Capturing Body)

A sensing element according to the present invention preferably has a capturing body for capturing a target substance in a specimen, on the surface of a metallic pattern. The capturing body to be used is a substance involved in selecting the target substance in the specimen, and includes, for instance, a substance (a so-called receptor) selectively and directly reacting with the target substance in the specimen, a substance involved in the reaction with the target substance (for instance, a substance selectively causing a catalytic action in the reaction with the target substance), and a substance which inactivates other substances than the target substance in the specimen. The capturing body may also simultaneously have a function involved in indicating the presence or absence and degree of detection, for instance, the function of reacting with the substance emitted from the receptor or with a remaining substance, and being colored. The capturing body to be used in the present invention includes an enzyme, a sugar chain, a catalyst, an antibody, an antigen, a gene and a color reagent, but is not limited to them.

Subsequently, a method for immobilizing or carrying these capturing bodies onto the surface of a metallic pattern will now be described. The above-described capturing body is immobilized or carried onto the surface of the metallic pattern, for instance, through a covalent bond, an ionic bond, adsorption, or the like. The method for immobilizing or carrying the capturing body onto the surface of the metallic pattern is not limited in particular, as long as it can adequately immobilize or carry the capturing body onto the surface of the metallic pattern while keeping its function.

When a bonding method is employed, it is acceptable to directly react and to bond a capturing body having a reactive group capable of directly reacting with the surface of a metallic pattern with and to the surface, or to react a cross-linking material capable of directly reacting with the surface of the metallic pattern with the surface, then further react the capturing body with the cross-linking material to bond the capturing body to the surface of the metallic pattern. For instance, when the metallic pattern includes gold, silver or copper, it can directly immobilize the capturing body having a thiol group or an amino group thereon. It is also possible to make a silane coupling agent having the thiol group and the amino group react with the surface of the metallic pattern, further make the capturing body bonded to the silane coupling agent, and thus make the surface of the metallic pattern carry the capturing body. When an adsorption method is employed, it is essential only that a combination having a suitable affinity is selected from combinations between the capturing body and the material of the metallic pattern. It is also possible to form the surface having the suitable affinity by temporarily modifying the surface of the metallic pattern, and then immobilize the capturing body thereon.

(Detecting Device)

In the next place, a detecting device according to the present invention will be described. The detecting device according to the present invention has a sensing element having the configuration, a light source for irradiating the sensing element with light, and a light-receiving element for detecting characteristics of the light reflected from or having transmitted through the sensing element. When bringing a specimen containing a target substance into contact with the sensing element, physical properties in the vicinity of a metallic pattern change. Accordingly, it becomes possible for the detecting device to detect a change of physical properties in the vicinity of the metallic pattern, by irradiating the sensing element with light and further detecting the light transmitted through or reflected from the sensing element. Particularly, in the present invention, it is possible to form a substrate and an electroconductive layer from an optically transparent material, and a detecting device, which detects the characteristics of the light having transmitted through the sensing element and shows a higher effect.

By the way, a target substance to be detected by a detecting device according to the present invention may be a substance to be detected itself, a component specifically contained in the substance to be detected, or one part of the component. For instance, when the substance is to be detected is protein, the target substance may be the protein itself, or may be a partial amino acid sequence, which is specific for the protein. Furthermore, the detecting device according to the present invention may be composed so as to detect the target substance by making a capturing body directly capture the target substance, or so as to indirectly detect the target substance by making a capturing body capture a substance derived from the target substance or another substance than the target substance, which show the presence of the target substance.

For instance, an object to be measured is not limited to a biological substance, and the size is not limited. However, a target substance is preferably a biological substance contained in an organism, such as sugar, protein, amino acid, antibody, antigen, para-antigen, vitamin and gene; a related substance thereof; and an artificially synthesized para-biological substance. It is also possible for the detecting device to complexly employ the above-described capturing bodies, so that a detecting device, such as a complexing enzyme sensor, an anti-body enzyme sensor and an enzyme-microbe hybrid sensor can be composed.

(Production of Sensing Element)

In the next place, a method for producing a sensing element according to the present invention will be described. The sensing element can be produced, for instance, by conducting the following step (A) to step (D).

<Step (A): step of preparing substrate having electroconductive layer>

A substrate having an electroconductive layer may be selected and used from a commercially available substrate, such as an ITO-coated glass substrate and an FTO-coated glass substrate, or may be prepared by forming an electroconductive layer on an arbitrary substrate. A usable method for forming the electroconductive layer includes a physical production method, such as a sputtering method and a vacuum evaporation technique, and a chemical production method, such as a spray method, a dipping method, a spin coating method and a CVD method.

<Step (B): step of forming an insulating layer on electroconductive layer>

An insulating layer is formed on a substrate so as to function as a mold used when forming a metallic pattern by electrolytic plating. Accordingly, an insulating material for forming the insulating layer has only to be a material having a capability of forming a region which is not electrolytically plated, on the substrate, in other words, the region in which the metallic pattern is not formed. A preferably used material for forming such an insulating layer includes a so-called photoresist material, an electron beam resist material and an X-ray resist material.

A production method according to the present invention can control sizes of metallic dots in a dot pattern and of hole-shaped cavities in a hole pattern to be formed, by controlling the sizes of regions in which an insulating material layer is removed in step (C). It is practically suitable for detection using a plasmon resonance method to control the size of the metallic dots and the hole-shaped cavities (opening), or the diameter when the cross section is circular, to 50 nm or larger, but 450 nm or smaller. When forming the metallic dots and the hole-shaped cavities (opening) into the above range of the size, a photoresist material is preferable as an insulating material, because it can be formed into a dot pattern or hole pattern with a size of 450 nm or smaller. A patterning technology, particularly with the use of an ArF, a KrF or an $F_2$ laser can form a pattern with several hundreds of nanometers or smaller, and a resist material, such as a fluorine base polymer to be used in them, is preferably used for the insulating material according to the present invention. A patterning technology using electron beam lithography similarly can form a fine pattern, so that the electron beam resist material used in the electron beam lithography is also preferable for the insulating material. A method of forming a mask in which the fine pattern is drawn and exposing a resist material to X-rays through the mask to form a pattern also can form the fine pattern, so that the X-ray resist material used for the method can be preferably used for the insulating material. As for such a fine patterning technology, many technologies are proposed including not only such a technology of a top-down system as is represented by photolithography, electron beam lithography and X-ray lithography, but also a technology of a bottom-up system, and they can be preferably applied to the present invention. For instance, a block polymer and a grafted polymer are preferably used for the insulating material, because the fine pattern can be formed by using phase separation peculiar to them. These polymers are formed of two or more polymer chains, and the fine pattern can be formed by selectively removing one or more polymer phases after having caused the phase separation.

An insulating layer is formed on an electroconductive layer through using these insulating materials. The insulating layer can be formed by applying the insulating material or a solution containing the insulating material onto the electroconductive layer, for instance, with a spin coating method, a dip coating method, or the like. As described above, the method of forming the layer with an application method is simple and preferable.

<Step (C): step of selectively removing a predetermined part of an insulating layer>

The present step exposes a predetermined part of the surface of an electroconductive layer, and forms a region in which a metallic pattern is formed in a step (D). For instance, when having employed a photoresist material for an insulating material in a step (B), the predetermined part of the insulating layer can be selectively removed by exposing the material through a mask and developing it. In addition, a method of using photolithographic technology as described above is preferable, because the method can control sizes of metallic dots and hole-shaped cavities, which will be formed later, and spacing between each of them, by using the mask. For instance, when using an electron beam resist for the insulating material in the step (B), and an electron beam lithographic method in the present step, a finer pattern can be directly drawn by directly exposing the resist to the electron beam without requiring the mask, as in the case of photolithography. In addition, for instance, when the X-ray resist is employed for the insulating material in step (B), the insulating layer can be patterned with the X-ray lithographic technology. If having formed the electron beam mask in which the fine pattern is drawn by electron beam exposure and employing the X-ray lithography technology of exposing a resist material to the X-rays, the fine pattern with a nanometer level can be formed, and, at the same time, productivity can be improved (shortening of production time) by using the mask. In addition, for instance, when having employed a block polymer, a grafted polymer, or the like, for the insulating material in step (B), it is possible to selectively remove the predetermined part of the insulating layer, by causing phase separation in a formed insulating layer and then selectively removing the phase-separated polymer phase. For the purpose of selectively removing the polymer phase, it is recommended to use a difference of characteristics between the separated polymer phases. For instance, it is possible to selectively remove the polymer phase, by using the difference of the characteristics, such as solubility, a pyrolytic property and a photolytic property. As described above, the method of using the phase separation of the block polymer or the grafted polymers is also simple, and further, less expensive and more preferable. By the way, in order to induce the phase separation, it is also acceptable to heat the insulating layer to a glass transformation temperature or higher after having formed the layer. In addition, when the electroconductive material layer is not exposed at the surface even after the insulating layer has been removed by using the difference of the above-described characteristics because of insufficient removal, it is acceptable to lightly etch the insulating layer with oxygen plasma.

<Step (D): step of forming a metallic pattern on substrate by an electrolytic plating method>

In the present step, a metallic pattern is formed on a region at which an insulating material is selectively removed in a step (C). In the present invention, an electrolytic plating method is employed in order to form the metallic pattern, so that the metallic pattern is selectively formed on the region as an initiation point, at which an electroconductive layer is exposed at the surface. A size and a shape of the metallic pattern can be controlled by appropriately selecting a current density and a plating period of time in electrolytic plating. Accordingly, an employment of a production method according to the present invention makes it possible to independently form each of metallic dots and hole-shaped cavities, and to improve the sensitivity and stability of a sensing element and a detecting device. It is also possible to temporarily prepare the metallic pattern and further electrolytically plating a metal on the metallic patterned layer as the initiation point of deposition, and to form the metallic pattern consisting of two or more material layers as well.

In addition, after the present step, all of or a part of a remaining insulating layer may be removed. The removal increases the surface area of a metallic pattern contactable with a specimen, and can contribute to the improved sensitivity of a sensing element and a detecting device.

A sensing element can be produced by carrying out the above-described step (A) to step (D).

EXAMPLES

Next, the present invention will be described further in detail with reference to examples, but the present invention is not limited to these examples, and a material, a composition condition, a reaction condition, and the like, can be freely changed in such a range as to be capable of providing a sensing element and a detecting device having a function to be aimed in the present invention.

Example 1

The present example is an example of having produced a sensing element by the steps of employing ITO for an electroconductive material, forming a metallic dot pattern made of gold on a substrate, and making the metallic dot carry an antibody of a capturing body. The present example employs a photolithographic technology, so that an obtained sensing element has a uniform size of and spacing between the metallic dots and shows adequate performance.

Figure 2A:
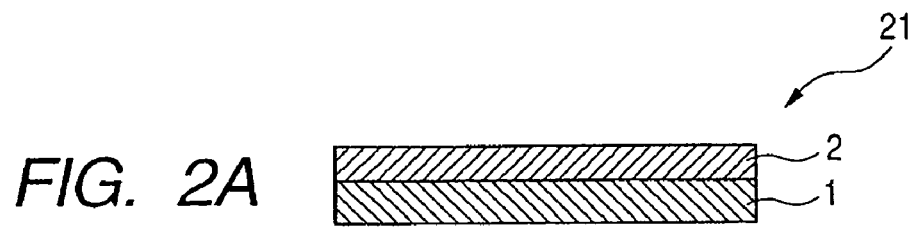
FIGS. 2A, 2B, 2C, 2D and 2E are views schematically showing a process for preparing metallic dots in Example 1.
Figure 2B:
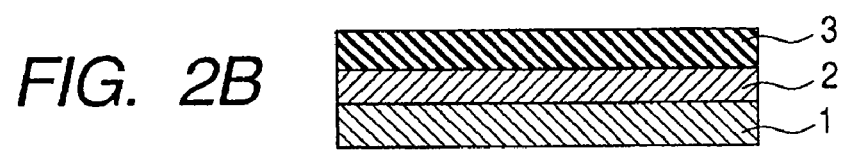
Figure 2C:
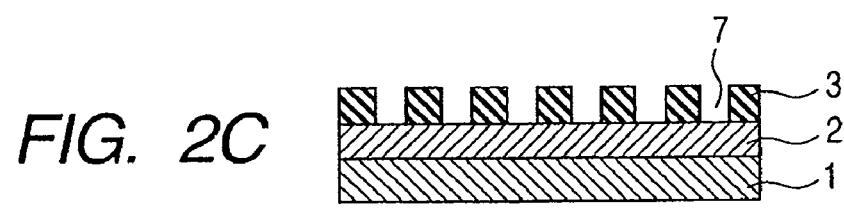
Figure 2D:
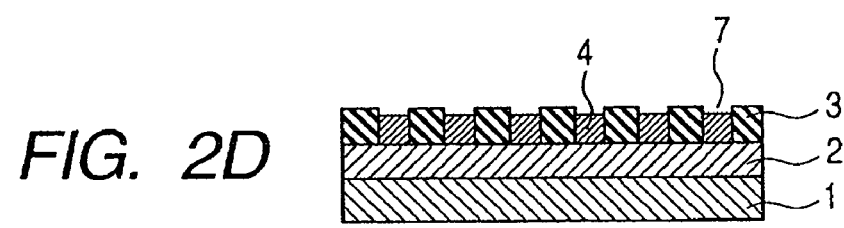
Figure 3A:
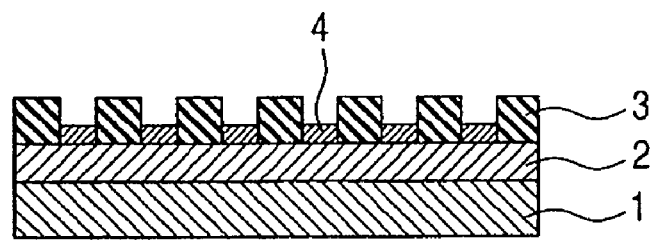
FIGS. 3A, 3B and 3C are schematic block diagrams showing a cross-sectional shape of an insulating layer and metallic dots, according to the present invention.
Figure 3B:
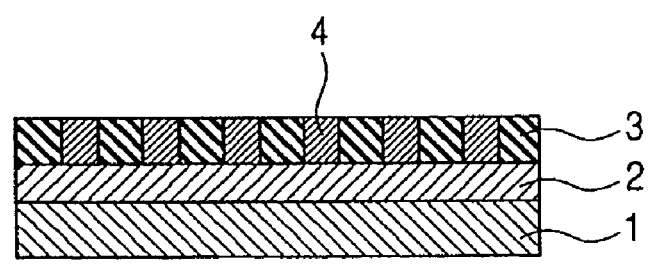
Figure 3C:
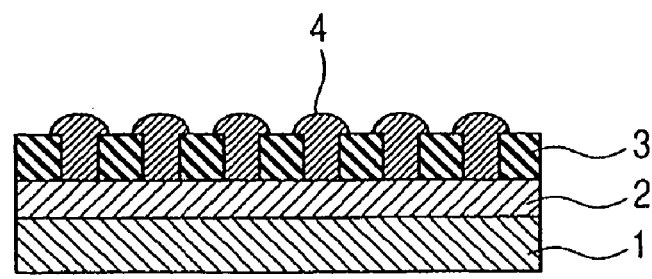

At first, as shown in FIG. 2A, form the film of ITO 2 on a glass substrate 1 with a sputtering method to prepare an ITO-coated glass substrate 21. The ITO-coated glass substrate 21 has a structure in which an electroconductive layer 2 is stacked on the substrate 1 shown in FIG. 2A. Subsequently, form a photoresist layer on the ITO layer formed on the glass substrate by using a photoresist material with a spin coating method, and pre-bake it to form an insulating layer 3 (FIG. 2B). Then, expose the insulating layer to light through a mask, and develop it to form a pattern in the insulating layer, in which a plurality of regions 7 are formed where a predetermined part of the insulating layer has been selectively removed (hereafter called a "removed region") (FIG. 2C). A shape of the removed region in the insulating layer in the present example is a cylindrical shape with a diameter of 100 nm, and the electroconductive layer is exposed at the bottom surface of the cylindrical shape. In addition, these removed regions are arranged at an equal spacing of 300 nm. Next, connect a power source (not shown) with an electroconductive layer, and immerse the substrate into a commercially-available electrolytic gold-plating solution. Then, apply a current density of 0.5 A/dm$^2$ to the electroconductive layer in an acidic bath (pH=4.5) kept at 40° C., to electrodeposit gold on the layer and form metallic dots made of gold (gold dots) in the removed regions formed in the insulating layer (FIG. 2D). The shape of the gold dot can be changed, by appropriately controlling current density and a plating period of time in the electrolytic plating. For instance, the gold dot 4 can be formed so as to have a thickness of the insulating layer or thinner, as is shown in FIG. 3A, and to have a disc shape. The disc-shaped metallic dot can increase the sensitivity of the sensing element. The gold dot 4 may also be formed so as to have approximately the same thickness as that of the insulating layer, as is shown in FIG. 3B. In the above step, when the insulating layer is thick, the metallic dot to be formed can increase its size and its surface area, and consequently, can increase an amount of a capturing body which will be carried on the dot later, and of a target substance to react with the capturing body. Furthermore, the metallic dot 4, even having overflowed on the insulating layer, as is shown in FIG. 3C, does not impair its effect in the present invention, so long as the metallic dot does not contact with or join with the adjacent metallic dot, and can be preferably used.

Subsequently, remove a photoresist layer by a peeling liquid or oxygen plasma, as needed.

Figure 2E:
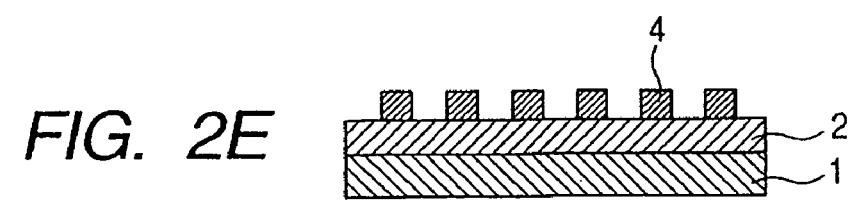

Through the above-described operation, metallic dots 4 made of gold with a uniform size are formed on an electroconductive material layer on a glass substrate at equal spacing, as is shown in FIG. 2E.

Subsequently, immobilize an antibody of a capturing body on a gold dot surface. In the present example, use a rabbit antimouse IgG antibody as the antibody. At first, apply an ethanol solution of 11-mercaptoundecanoic acid having a thiol group onto a glass substrate. By the operation, a carboxyl group is immobilized and exposed at the gold dot surface. Subsequently, apply an aqueous solution of N-hydroxysulfosuccinimide (product made by Dojindo Laboratories Corporation) and an aqueous solution of 1-ethyl-3-[3-dimethylamino]propyl]carbodiimide hydrochloride (product made Dojindo Laboratories Corporation), in a similar way. By these operations, a succinimide group is exposed at the gold dot surface. Subsequently, immerse the glass substrate into a buffer solution (pH 8.0) of rabbit antimouse IgG antibody/tris-hydrochloric acid. Then, the succinimide group formed on the gold dot surface reacts with the amino group of the rabbit antimouse IgG antibody, and the rabbit antimouse IgG antibody is immobilized on the gold dot surface.

Through the above-described operation, a sensing element can be produced, which has a rabbit antimouse IgG antibody as a capturing body.

In the next place, an example of a detecting device provided with the sensing element produced by the above-described operation will be described. The present example describes an example of detecting a target substance with light having passed through the sensing element. FIG. 4A schematically shows the detecting device according to the present example. The detecting device is provided with the sensing element 40, a light source 8 and a light-receiving element 11. In the present example, a xenon lamp is used for the light source, but the light source is not limited to it, as long as the light source can emit a light including a wavelength region which causes a characteristic change before and after the application of a specimen, such as a halogen lamp and a mercury lamp. In addition, the light source 8 during detection is placed at such a position as to be able to irradiate a metallic dot 4 in the sensing element with a measuring light 9, as is schematically shown in FIG. 4A, and the light-receiving element 11 is placed at such a position as to be able to detect the characteristics of the measuring light 10 having passed through the sensing element 40. In the present example, a photodiode of silicon is used for the light-receiving element, but the light-receiving element is not limited to it, as long as the light-receiving element can receive the light with the wavelength region which causes a characteristic change before and after the application of a specimen, such as a photomultiplier. In addition to the above components, a spectrophotometric detector, which is not shown in the figure, may be provided in the light-receiving element. Furthermore, the detecting device is preferably provided with an arithmetic unit for calculating the detected characteristic change, displaying means for displaying a detection result, and the like, which are not shown in the figure.

Subsequently, an example of sensing a target substance with the use of a produced detecting device will be described. At first, arrange a sensing element, a light source and a light-receiving element into a positional relationship for the above-described detection, and detect the spectrum. Then, apply a specimen made of a phosphate buffer solution containing mouse IgG as a target substance to the sensing element, bring the specimen into contact with the sensing element, and make the specimen react with a capturing body immobilized on gold dots. It is acceptable to clean a metallic dot surface with the phosphate buffer solution, after the reaction. Subsequently, again, arrange the sensing element, the light source and the light-receiving element into the positional relationship for the above-described detection, and detect the spectrum. A change of the spectrum before and after the application of a specimen is caused by the change of a plasmon resonant state of the gold dot, and means that the antigen-antibody reaction occurred on the sensing element, and that the capturing body captured the target substance. Thereby, it becomes possible to sense the target substance in the specimen, by detecting the change of the spectrum.

In addition, here, previously acquire the relation between the change of the spectrum and the concentration of a target substance by using known normal specimens of a plurality of concentrations; and determine a working curve on the basis of the relation to determine a function of the change of the spectrum and the concentration. Then, by using the function, the concentration of the target substance can be determined from the change of the spectrum obtained in real measurement.

As for a change of a spectrum described above, the change of the spectrum may be the change of a spectrum peak at a wavelength having a maximum value, or may be the change of a peak shape, such as a half width of a spectral peak waveform. Furthermore, the change of a spectrum may be the change of light intensities at one or more wavelength points.

As described above, it becomes possible through the present invention to detect a target substance in a specimen at a sufficient sensitivity.

Example 2

The present example describes an example of having produced a sensing element by the steps of employing ITO for an electroconductive material and a block polymer for an insulating material, forming a metallic dot pattern made of gold on a substrate, and making the metallic dot carry an antibody of a capturing body. When having used the block polymer for an insulating layer, the metallic dot with a fine size can be easily formed.

Figure 5A:
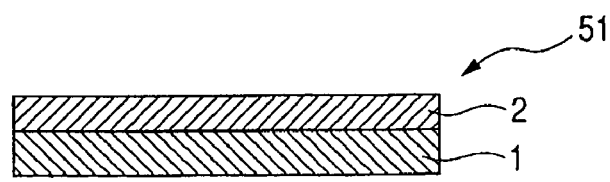
FIGS. 5A, 5B, 5C, 5D and 5E are views schematically showing a process for preparing metallic dots in Example 2.
Figure 5B:
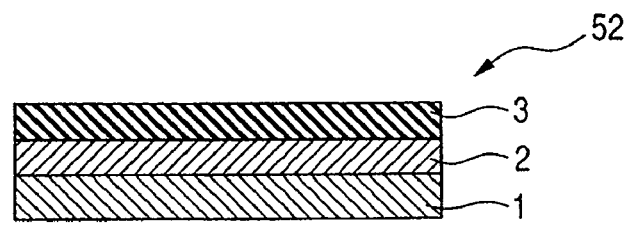
Figure 5C:
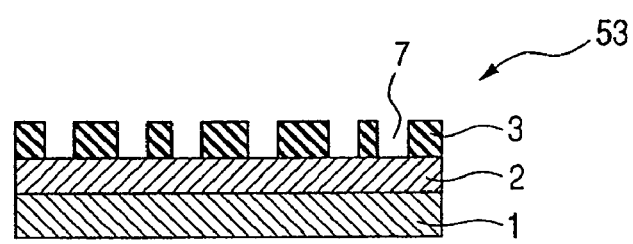

At first, prepare an ITO-coated glass substrate 51 (FIG. 5A) as in the case of Example 1. Subsequently, prepare a toulene solution of PS-b-MMA (polystyrene-methyl methacrylate copolymer) (product made by Sowa Kagaku Co., Ltd.), which is a commercially-available block polymer, apply the solution onto an ITO layer 2 (electroconductive layer) formed on a glass substrate 1, and spin-coat it to form an insulating layer 3 (FIG. 5B). Heat a provided structure 52 to 150° C. to induce the phase separation of the block polymer. Subsequently, selectively decompose and remove MMA by dry-etching the structure 52, or by irradiating it with a UV light and then immerse it in acetic acid. Then, the insulating layer 3 is partially removed, and a plurality of removed regions 7 are formed in which the electroconductive layer 2 is exposed at a bottom part (FIG. 5C). The shape of the removed region 7 in the present example is a cylindrical shape with a diameter of 50 nm.

Figure 5D:
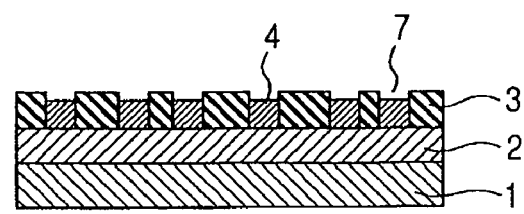

Subsequently, connect a power source (not shown) with the electroconductive layer, and immerse the obtained structure 43 in a commercially-available gold-electroplating liquid. Then, apply a current density of 0.5 A/dm$^2$ to the electroconductive layer in an acidic bath (pH=4.5) kept at 40° C., to electrodeposit gold on the layer and form gold dots in the removed regions (FIG. 5D). Subsequently, remove an insulating layer 3 by dry etching.

Figure 5E:
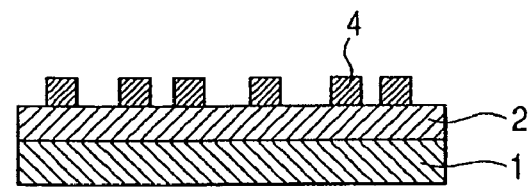

Through the above-described operation, metallic dots 4 made of gold (gold dots) with an approximately uniform size, as shown in FIG. 5E, are formed on an electroconductive material layer on a glass substrate.

Subsequently, immobilize a rabbit antimouse IgG antibody as a capturing body on a gold dot surface with the same method as in the case of Example 1, to produce a sensing element.

Next, an example of a detecting device provided with the sensing element produced by the above-described operation will be described. The present example describes an example of detecting a target substance with light reflected from a sensing element. FIG. 4B schematically shows the detecting device according to the present example. The detecting device is provided with the sensing element 40, a light source 8 and a light-receiving element 11. The light source 8 during detection is placed at such a position so as to be able to irradiate a gold dot 4 in the sensing element 40 with a measuring light 9, as is schematically shown in FIG. 4B, and the light-receiving element 11 is placed at such a position so as to be able to detect the characteristics of the measuring light 10 reflected from the sensing element 40. In addition to the above components, a spectrophotometric detector, which is not shown in the figure, may be provided in the light-receiving element 11. Furthermore, the detecting device is preferably provided with an arithmetic unit for calculating the detected characteristic change, displaying means for display a detection result, and the like, which are not shown in the figure.

Subsequently, an example of sensing a target substance with the use of a produced detecting device will be described. At first, arrange a sensing element, a light source and a light-receiving element into a positional relationship for the above-described detection, and detect the spectrum. Then, apply a specimen made of a phosphate buffer solution containing mouse IgG to the sensing element as a target substance, bring the specimen into contact with the sensing element, and make the specimen react with a capturing body. It is acceptable to clean a metallic dot surface with the phosphate buffer solution, after the reaction. Subsequently, again, arrange the sensing element, the light source and the light-receiving element into the positional relationship for the above-described detection, and detect the spectrum. A change of the spectrum before and after the application of a specimen is caused by the change of a plasmon resonant state of the gold dot, and means that the antigen-antibody reaction occurred on the sensing element, and that the capturing body captured the target substance. Thereby, it becomes possible to sense the target substance in the specimen, by detecting the change of the spectrum.

The concentration of a target substance can also be determined by determining a working curve as in the case of Example 1. The change of the spectrum may be the change of a wavelength having a spectrum peak, may be the change of a peak shape, or further may be the change of light intensities at one or more wavelength points.

As described above, it becomes possible through the present invention to detect a target substance in a specimen at a sufficient sensitivity.

Example 3

The present example is an example of having produced a sensing element by the steps of employing ITO for an electroconductive material, forming a metallic dot pattern made of two layers of gold and silver on a substrate, and making the metallic dot carry a plurality of antibodies as a capturing body. In the present example, the metallic dot is composed of the two metallic layers, which can contribute to both an increase in sensitivity and improvement in corrosion resistance.

Figure 6A:
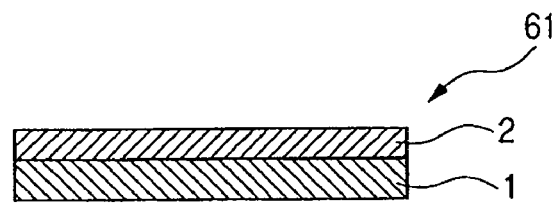
FIGS. 6A, 6B, 6C, 6D, 6E and 6F are views schematically showing a process for preparing metallic dots in Example 3.
Figure 6B:
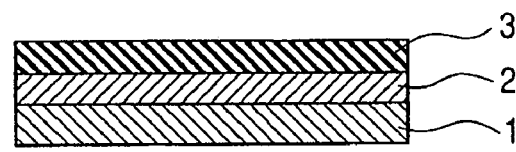
Figure 6C:
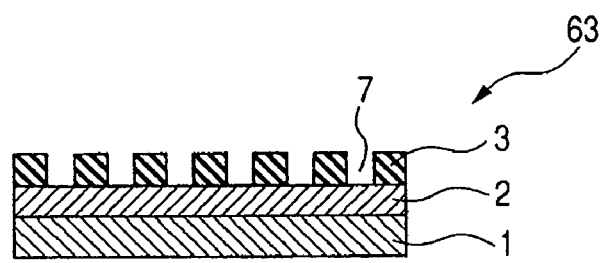

At first, prepare an ITO-coated glass substrate 61 (FIG. 6A) as in the case of Example 1. Subsequently, form a photoresist layer on the ITO layer 2 (electroconductive layer) formed on a glass substrate 1 by using a photoresist material with a spin coating method, and pre-bake it to form an insulating layer 3 (FIG. 6B). Subsequently, expose the insulating layer 3 to light through a mask, and develop it to form a pattern in the insulating layer 3. Thus, a plurality of removed regions 7 are formed in which the electroconductive layer 2 is exposed at the bottom part (FIG. 6C). The shape of the removed region 7 in the present example is a cylindrical shape with a diameter of 100 nm, and these removed regions are arranged at an approximately equal spacing of 400 nm.

Subsequently, connect a power source (not shown) with an electroconductive layer, and immerse the obtained structure 63 in a commercially-available silver-electroplating liquid.

Figure 6D:
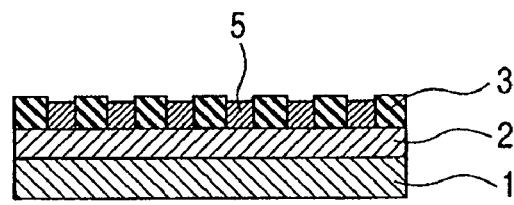

Then, apply a current density of 1 A/dm$^2$ to the electroconductive layer 2 in an alkaline bath (pH=12) kept at 45° C., to electrodeposit silver on the layer and form a metallic layer 5 (silver dots) made of silver in the hole (FIG. 6D). Immerse the obtained structure 65 in a commercially-available gold-electroplating liquid to electroplate gold on the structure. Then, gold is deposited on the silver dot 5 to form a metallic layer 6 made of gold. It is recommended to appropriately set electrolytic plating conditions, such as current density and a plating period time, so that adjacent metallic dots do not come into contact with each other by two electroplating steps.

Figure 6E:
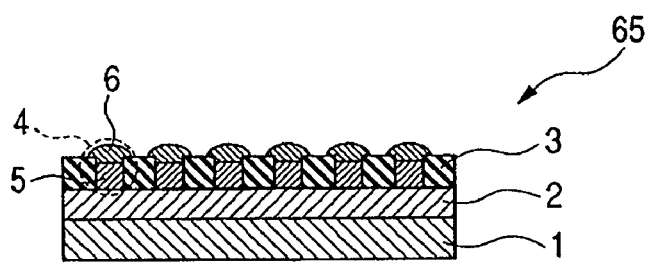
Figure 6F:
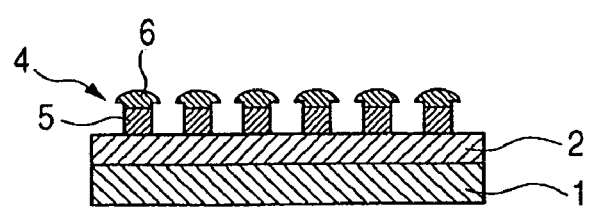

Through the above-described operation, metallic dots 4 formed of two layers of gold 6 and silver 5 (gold/silver dot) with an approximately uniform size, as shown in FIG. 6E, are formed at approximately equal spacing, on an electroconductive material layer on a glass substrate.

Figure 7:
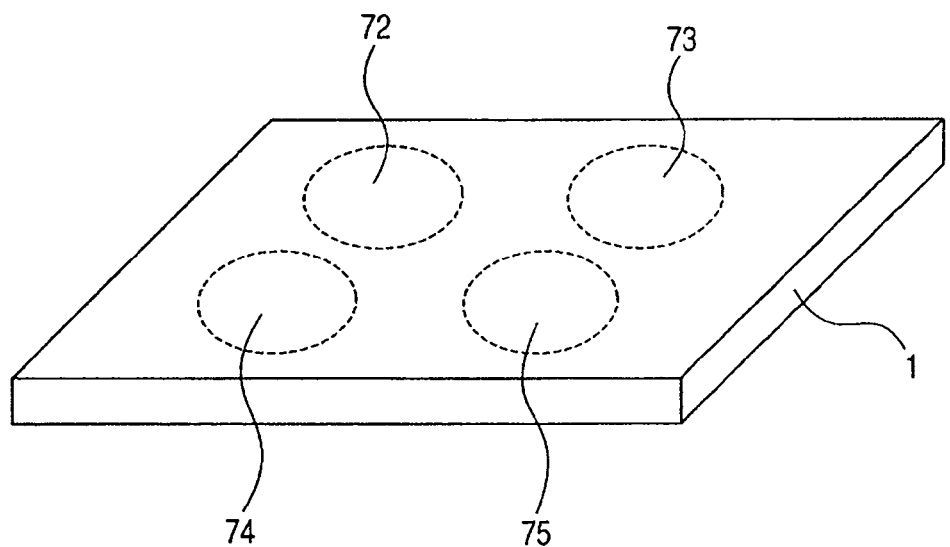
FIG. 7 is a schematic block diagram showing an example of a reaction zone on a substrate, according to Example 3.

Subsequently, immobilize an antibody of a capturing body on a metallic dot surface. Antibodies to be employed in the present example are an anti-CEA antibody, and an anti-AFP antibody, an anti-PSA antibody and an anti-PAP antibody. At first, apply an ethanol solution of 11-mercaptoundecanoic acid onto the metallic dot to modify the surface. In the step, drop a predetermined amount of a solution only on a reaction region with the use of a spotter, or the like, as is shown in FIG. 7. Thereby, a carboxyl group is exposed at the surface of the metallic dot. In the state, drop an aqueous solution of N-Hydroxysulfosuccinimide (made by Dojindo Laboratories Corporation) and an aqueous solution of 1-Ethyl-3 [3-dimethylamino]propyl]carbodiimidehydrochloride (made by Dojindo Laboratories Corporation) onto the reaction region similarly with the use of a spotter, or the like. Thereby, a succinimide group is exposed at the surface of the metallic dot. Furthermore, couple streptavidin with the succinimide group to modify the surface of the metallic dot with the streptavidin. Immobilize a biotin-modified antibody on the metallic dot. In the above step, apply each of an anti-CEA antibody, an anti-AFP antibody, an anti-PSA antibody and an anti-PAP antibody, to each of the reaction regions A to D shown in FIG. 7, and immobilize them.

Next, an example of a detecting device provided with the sensing element produced by the above-described operation will be described. The present example describes an example of detecting a target substance by light having passed through the sensing element. The detecting device according to the present example is provided with a light source and a light-receiving element, with respect to a reaction region of the sensing element. The light source during detection is placed at such a position so as to be able to irradiate a metallic dot 4 in the reaction region in the sensing element 40 with a measuring light 9, as is schematically shown in FIG. 4A, in a similar way in Example 1. The light-receiving element 11 is placed at such a position as to be able to detect the characteristics of the measuring light 10 having passed through the sensing element 40. In addition to the above components, a spectrophotometric detector, which is not shown in the figure, may be provided in the light-receiving element 11. Furthermore, the detecting device is preferably provided with an arithmetic unit for calculating the detected characteristic change, displaying means for displaying a detection result, and the like, which are not shown in the figure.

In the present example, detection is performed in a plurality of reaction regions. Accordingly, a light source and a sensing element may be arranged in each of the reaction regions. However, it is more preferable to prepare moving means for placing each of the reaction regions at detectable positions with respect to the light source and the light-receiving element, or reverse moving means for placing the light source and a light-receiving element at detectable positions with respect to each of the reaction regions. Alternatively, it is also acceptable to prepare means for refracting a measuring light to a detectable direction with respect to each of the reaction regions.

Subsequently, an example of a detecting method with the use of a produced detecting device will now be described. At first, arrange a sensing element, a light source and a light-receiving element into a positional relationship for the above-described detection, and detect the spectrum. Then, apply a specimen made of a phosphate buffer solution containing CEA to the substrate as a target substance, bring the specimen into contact with the sensing element, and make the specimen react with a capturing body, with the same method as in Example 1. It is recommended to clean the sensing element with the phosphate buffer solution, after the reaction. Subsequently, arrange the sensing element, the light source and the light-receiving element into the positional relationship similar to the above-described detection, and detect the spectrum from each of the reaction regions. Furthermore, make respective phosphate buffer solutions containing AFP, PSA and PAP as target substances react with each capturing body, clean the sensing element, and detect the spectrum, in a similar way to the above.

A change of the spectrum before and after applying the specimen is caused by the change of a plasmon resonant state of the metallic dot, and means that the antigen-antibody reaction occurred on the sensing element, and that the capturing body captured the target substance. Accordingly, when preparing a plurality of reaction regions on a sensing element and making respective reaction regions carry different capturing bodies, as in the present example, and when respective antigen-antibody reactions have occurred, a change of a spectrum corresponding to a respective reaction is observed in the respective reaction region. In addition, when having applied a plurality of the antigens simultaneously, the respective reaction region also reacts with the antigen, so that the change of the spectrum can be observed.

As described above, it becomes possible through the present invention to detect a plurality of target substances in a specimen at a sufficient sensitivity.

Example 4

The present example is an example of having produced a sensing element by the steps of employing ITO for an electroconductive material, forming a metallic dot pattern made of two layers of silver and gold on a substrate, removing an insulating layer, and then making the metallic dot carry an antibody as a capturing body. It is further an example of producing a detecting device provided with the sensing element, and of continuously detecting a target substance. The present example makes the insulating layer removed, and accordingly can increase the effective surface area of the metallic dot, which is exposed to a specimen. It is also possible to make the detecting device even micro-chipped, by applying the present invention into a channel.

At first, prepare an ITO-coated glass substrate as in the case of Example 1, form an insulating layer from a photoresist material, and pattern the insulating layer with a photolithographic method to form a plurality of removed regions. In the above step, form the removed regions in the region to be the reaction region in a channel later. Furthermore, electrolytically plate the removed regions with silver and subsequently, with gold in the same way as in Example 3, to form a metallic dot 4 (silver/gold dot) formed of two layers of silver 5 and gold 6, as is shown in FIG. 6E. Furthermore, remove an insulating 3 (photoresist layer) with a peeling liquid or oxygen plasma.

Through the above-described operation, metallic dots 4 made of gold 6 and silver 5 (gold/silver dot) with an approximately uniform size, as shown in FIG. 6E, are formed at approximately equal spacing, on an electroconductive material layer on a glass substrate.

Figure 8A:
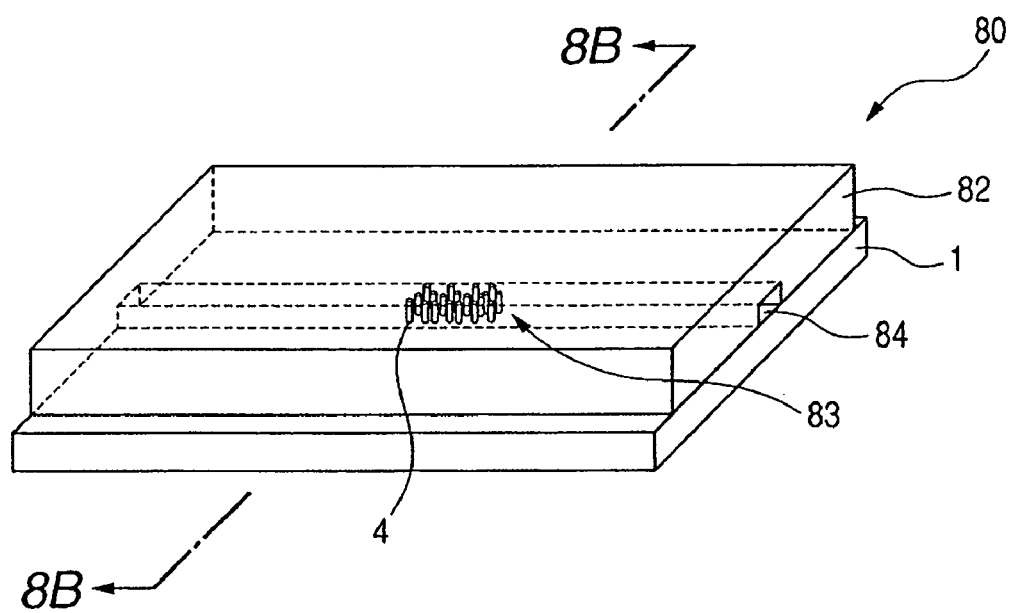
FIGS. 8A and 8B are schematic block diagrams showing an example of a detecting device, according to Example 4.
Figure 8B:
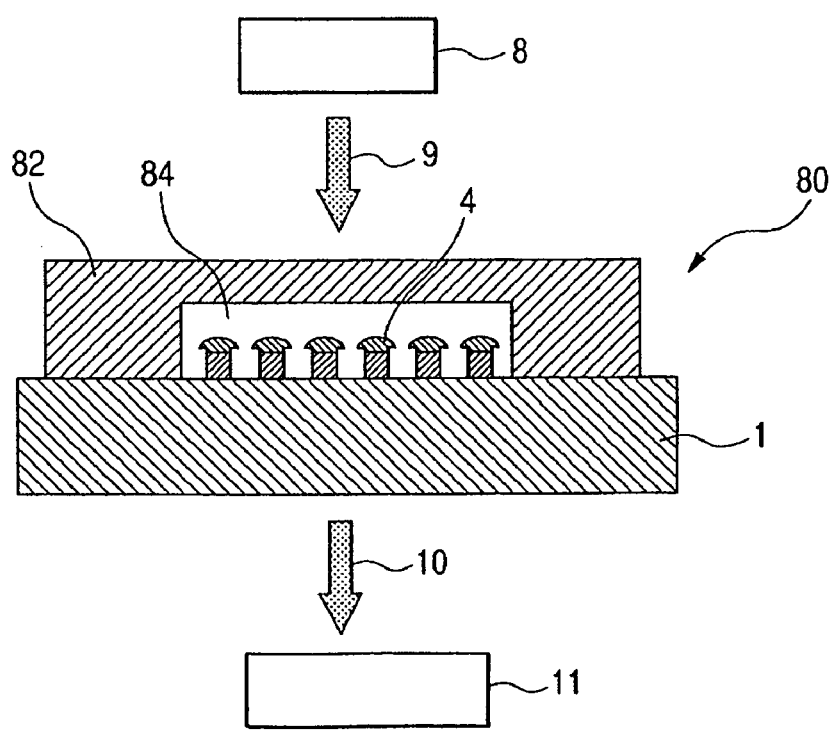

Subsequently, fix a cover made of a resin provided with a flute on a glass substrate to produce a channel. At this time, arrange a cover 82, a substrate 1 and a reaction region 83 so that the reaction region 83 having a metallic dot 4 formed thereon can be placed in the channel 84, as is shown in FIGS. 8A and 8B, to produce a sensing element 80.

Subsequently, immobilize an antibody of a capturing body on a metallic dot surface. In the present example, use a rabbit antimouse IgG antibody for an antibody, as in the case of Example 1. Immobilize the antibody, by sequentially passing the same ethanol solution of 11-mercaptoundecanoic acid, aqueous solution of N-hydroxysulfosuccinimde, aqueous solution of ethyl-3-3-dimethylaminopropylcarbodiimide hydrochloride, and buffer solution of rabbit antimouse IgG antibody/tris-hydrochloric acid as in the case of Example 1, through a channel.

Through the above-described operation, a sensing element can be produced, which has a rabbit antimouse IgG antibody as a capturing body.

Next, an example of a detecting device provided with the sensing element produced by the above-described operation will be described. The present example describes an example of detecting a target substance from light having passed through the sensing element.

FIGS. 8A and 8B are views schematically showing a detecting device according to the present example, FIG. 8A is a perspective view and FIG. 8B is a schematic block diagram of a detecting device, which includes a sectional view in 8B-8B of a sensing element 80 in FIG. 8A. The detecting device is provided with a light source 8 and a light-receiving element 11 with respect to the sensing element 80. Accordingly, the light source 8 during detection is placed at such a position so as to be able to irradiate a metallic dot 4 in the sensing element 80 with a measuring light 9, as is schematically 7 shown in FIG. 8B. The light-receiving element 11 is placed at such a position so as to be able to detect the characteristics of the measuring light 10 having passed through the sensing element 80. In addition to the above components, a spectrophotometric detector, which is not shown in the figure, may be provided in the light-receiving element. Furthermore, the detecting device is preferably provided with an arithmetic unit for calculating the detected characteristic change, displaying means for displaying a detection result, means for applying a specimen liquid into a channel, such as a pump, and the like, which are not shown in the figure.

Subsequently, an example of a detecting method with the use of a produced detecting device will now be described. At first, arrange a sensing element, a light source and a light-receiving element into a positional relationship for the above-described detection, and detect the spectrum. Then, introduce and supply a specimen formed of the same phosphate buffer solution containing mouse IgG as was used in Example 1 into a channel, bring the specimen into contact with the sensing element, and make the specimen react with a capturing body. Subsequently, arrange the sensing element, the light source and the light-receiving element into the positional relationship for the above-described detection, and detect the spectrum. A change of the spectrum before and after applying the specimen is caused by the change of a plasmon resonant state of the metallic dot, and means that the antigen-antibody reaction occurred on the sensing element, and that the capturing body captured the target substance. In addition, the concentration of a target substance can be determined by determining a working curve as in the case of Example 1. The change of the spectrum may be the change of a wavelength having a spectrum peak, may be the change of a peak shape, or further, may be the change of light intensities at one or more wavelength points, as in the case of Example 1. In addition, a sensing element according to the present invention is configured so as to be placed in the channel and, accordingly, can detect a change with time and the change of a reacting weight by continuing detection while supplying the liquid.

As described above, it becomes possible through the present invention to detect a target substance in a specimen even in a channel, at a sufficient sensitivity.

Example 5

The present example is an example of having produced a sensing element by the steps of employing a silver thin film for an electroconductive material, forming a metallic dot pattern formed of two layers of gold and silver on a substrate, and making the metallic dot carry antibodies of a capturing body. It is further an example of producing a detecting device provided with the sensing element and detecting a target substance. The present example makes an electroconductive layer to be one part of the metallic dot, and thereby makes it possible to improve the transparency of the substrate while maintaining the sensitivity of the sensing element.

Figure 9A:
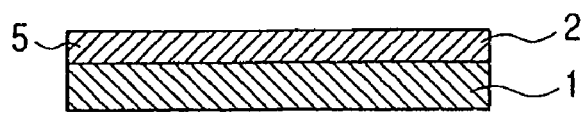
FIGS. 9A, 9B, 9C, 9D, 9E and 9F are views schematically showing a process for preparing metallic dots in Example 5.
Figure 9B:
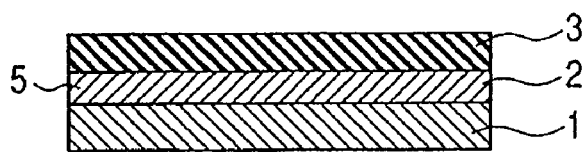
Figure 9C:
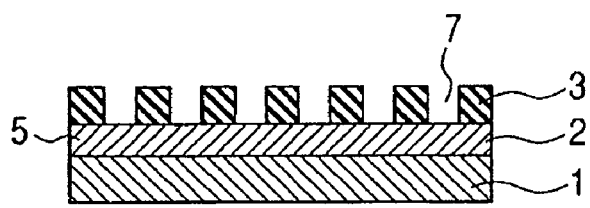
Figure 9D:
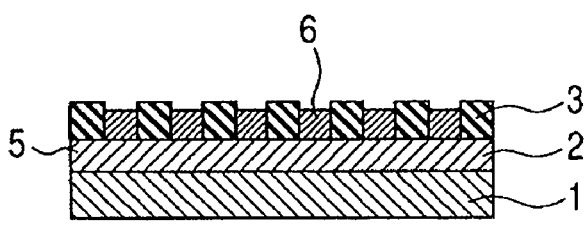
Figure 9E:
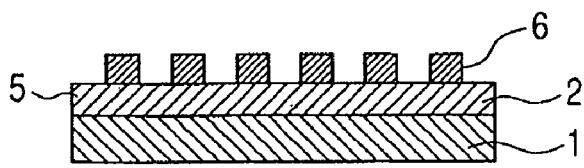

At first, form a silver thin film 2 on a glass substrate 1 (FIG. 9A). As a film-forming method, a general method, such as vapor deposition, can be applied. Subsequently, form an insulating layer 3 (FIG. 9B) from a photoresist material on a silver thin film 5, namely, an electroconductive layer 2 on a glass substrate 1, as in the case of Example 1, and pattern the insulating layer 3 with a photolithographic method to form a plurality of removed regions 7 in the insulating layer 3 (FIG. 9C). Furthermore, electrolytically plate gold in the removed regions to form a metallic layer 6 (FIG. 9D), as in the case of Example 1, and subsequently, remove the insulating layer 3 (FIG. 9E) with a peeling liquid or oxygen plasma as in the case of Example 1. Subsequently, etch the electroconductive layer 2. In the present example, because the metallic layer 6 is gold and the electroconductive layer 2 is silver, it is possible to selectively etch and remove a part exposed at a removed region 7 out of the electroconductive layer 2 made of silver, by making use of a difference of etching resistance between gold and silver, and using the metallic layer 6 made of gold as a mask.

Figure 9F:
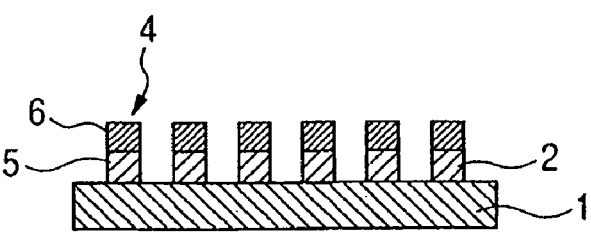

Through the above-described operation, metallic dots 4 made of gold 6 and silver 5 (gold/silver dot) with an approximately uniform size, as shown in FIG. 9F, are formed at approximately equal spacing, on an electroconductive layer 2 on a glass substrate 1.

Subsequently, immobilize an antibody of a capturing body on a metallic dot surface. In the present example, an anti-AFP (a-fetoprotein) antibody is used as the antibody. At first, modify the surface of the metallic dot to form a carboxyl group on the surface, by using 11-mercaptoundecanoic acid, with the same method as in Example 1. Subsequently, apply an aqueous solution of N-hydroxysulfosuccinimide (product made by Dojindo Laboratories Corporation) and an aqueous solution of 1-ethyl-3-3-dimethylaminopropylcarbodiimide hydrochloride (product made by Dojindo Laboratories Corporation), onto the surface, thereby to expose a succinimide group on the surface of the metallic dot. Furthermore, couple streptavidin with the succinimide group to modify the surface of the metallic dot with streptavidin. Immobilize a biotinylated anti-AFP antibody on the metallic dot.

Through the above-described operation, a sensing element can be produced, which has an anti-AFP antibody as a capturing body.

Next, an example of a detecting device provided with the sensing element produced by the above-described operation will be described. The present example describes an example of detecting a target substance from light having passed through the sensing element.

The detecting device according to the present example is provided with a light source and a light-receiving element, with respect to a reaction region of the sensing element. The light source during detection is placed at such a position so as to be able to irradiate a metallic dot 4 in the sensing element 40 with a measuring light 9, as is schematically shown in FIG. 4A, in a similar way to Example 1. The light-receiving element 11 is placed at such a position so as to be able to detect the characteristics of the measuring light 10 having passed through the sensing element 40. In addition to the above components, a spectrophotometric detector, which is not shown in the figure, may be provided in the light-receiving element. Furthermore, the detecting device is preferably provided with an arithmetic unit for calculating the detected characteristic change, displaying means for displaying a detection result, and the like, which are not shown in the figure.

Subsequently, an example of sensing a target substance with the use of a produced detecting device will be described. At first, arrange a sensing element, a light source and a light-receiving element into a positional relationship for the above-described detection, and detect the spectrum. Then, apply a specimen made of a phosphate buffer solution containing AFP to the sensing element as a target substance, bring the specimen into contact with the sensing element, and make the specimen react with a capturing body. It is acceptable to clean a metallic dot surface with the phosphate buffer solution, after the reaction. Subsequently, arrange the sensing element, the light source and the light-receiving element into the positional relationship for the above-described detection, and detect the spectrum. A change of the spectrum before and after applying the specimen is caused by the change of a plasmon resonant state of the metallic dot, and means that the antigen-antibody reaction occurred on the sensing element, and that the capturing body captured the target substance. Thereby, it becomes possible to sense the target substance in the specimen, by detecting the change of the spectrum.

In addition, the concentration of a target substance can be determined by determining a working curve as in the case of Example 1. The change of the spectrum may be the change of a wavelength having a spectrum peak, may be the change of a peak shape, or further, may be the change of light intensities at one or more wavelength points, as in the case of Example 1.

As described above, it becomes possible through the present invention to detect a target substance in a specimen at a sufficient sensitivity.

Example 6

The present example is an example of having produced a sensing element by the steps of forming a hole pattern made of gold on a substrate, and making the metallic pattern carry an antibody of a capturing body. The present example employs a photolithographic technology so that an obtained sensing element has a uniform size of and spacing between the hole-shaped cavities (opening) and shows adequate performance.

Figure 11A:
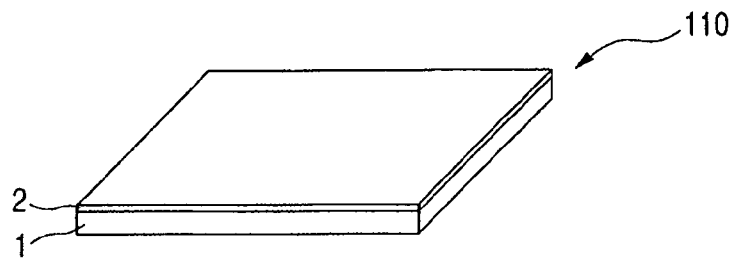
FIGS. 11A, 11B, 11C, 11D and 11E are views schematically showing a process for preparing a hole pattern of metal in Example 6.
Figure 11B:
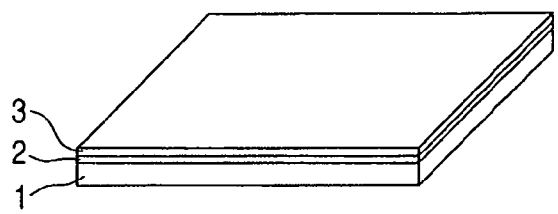
Figure 11C:
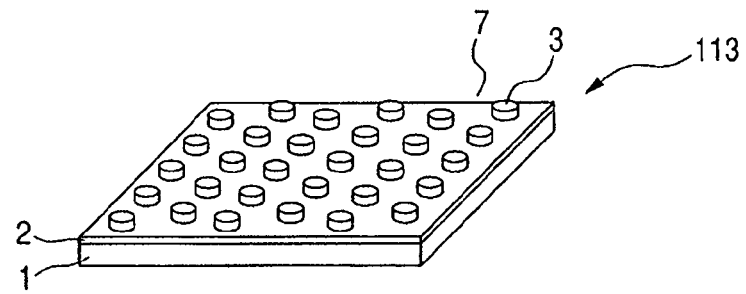

At first, prepare an ITO-coated glass substrate 110 (FIG. 11A), as in the case of Example 1. Subsequently, form an insulating layer 3 on the ITO layer 2 formed on the glass substrate 1 by using a photoresist material (FIG. 11B), as in the case of Example 1. Then, expose the insulating layer 3 to light through a mask, and develop it to form a pattern in the insulating layer, in which a plurality of regions 3 (hereafter called an insulating region) are formed, each of which is formed of an independent insulating layer, as is shown in FIG. 11C. Here, the shape of the insulating region 3 in the present example is a cylindrical shape with a diameter of 200 nm, and the electroconductive layer 2 is exposed at the bottom of the removed region 7 surrounding them. In addition, these insulating regions 3 are placed at an equal spacing of 300 nm.

Figure 11D:
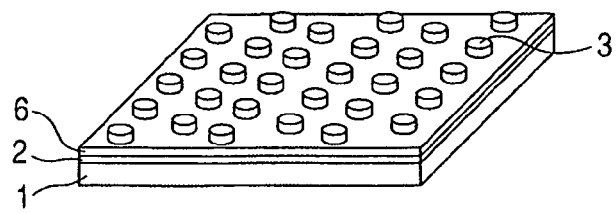

Subsequently, connect a power source (not shown) with an electroconductive layer 2, and immerse the obtained structure 113 in a commercially-available gold-electroplating liquid, as in the case of Example 1. Then, apply a current density of 0.5 A/dm$^2$ to the electroconductive layer 2 in an acidic bath (pH=4.5) kept at 40° C., to electrodeposit gold on the layer and form a metallic layer 6 made of gold in the removed region (FIG. 11D). Subsequently, remove the insulating layer 3 by a peeling liquid or oxygen plasma.

Figure 11E:
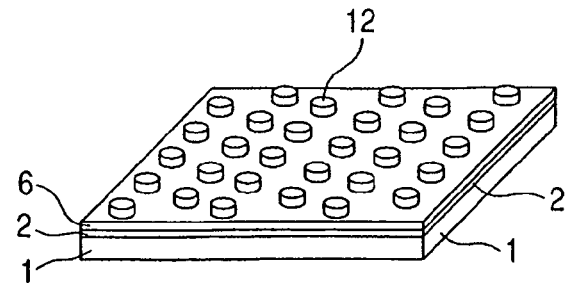

Through the above-described operation, holes 12 with a uniform size are formed on an electroconductive layer 2 on a glass substrate 1 at equal spacing, and a hole pattern 6 made of gold is formed on the layer, as is shown in FIG. 11E.

Subsequently, immobilize a rabbit antimouse IgG antibody as a capturing body on the surface of gold in the hole pattern with the same method as in the case of Example 1, to produce a sensing element.

Next, an example of a detecting device provided with the sensing element produced by the above-described operation will be described. The present example describes an example of detecting a target substance from light having passed through the sensing element.

The detecting device according to the present example is provided with a light source and a light-receiving element, with respect to a reaction region of the sensing element. The light source during detection is placed at such a position so as to be able to irradiate a gold pattern in the sensing element with a measuring light, in the same way as in Example 1. The light-receiving element is placed at such a position so as to be able to detect the characteristics of the measuring light have passed through the sensing element. In addition to the above components, a spectrophotometric detector, which is not shown in the figure, may be provided in the light-receiving element. Furthermore, the detecting device is preferably provided with an arithmetic unit for calculating the detected characteristic change, displaying means for displaying a detection result, and the like, which are not shown in the figure.

Subsequently, an example of sensing a target substance with the use of a produced detecting device will be described. At first, arrange a sensing element, a light source and a light-receiving element into a positional relationship for the above-described detection, and detect the spectrum. Then, apply a specimen made of a phosphate buffer solution containing mouse IgG to the sensing element as a target substance, bring the specimen into contact with the sensing element, and make the specimen react with a capturing body. It is recommended to clean the surface of a metallic pattern with the phosphate buffer solution, after the reaction. Subsequently, arrange the sensing element, the light source and the light-receiving element into the positional relationship for the above-described detection, and detect the spectrum. A change of the spectrum before and after applying the specimen is caused by the change of a plasmon resonant state of the metallic pattern, and means that the antigen-antibody reaction occurred on the sensing element, and that the capturing body captured the target substance. Thereby, it becomes possible to detect the target substance in the specimen, by detecting the change of the spectrum.

In addition, the concentration of a target substance can be determined by determining a working curve, as in the case of Example 1. The change of the spectrum may be the change of a wavelength having a spectrum peak, may be the change of a peak shape, or further may be the change of light intensities at one or more wavelength points, as in the case of Example 1.

As described above, it becomes possible through the present invention to detect a target substance in a specimen at a sufficient sensitivity.

What is claimed is:

1. A method of producing a sensing element used in a detecting device for detecting a target substance in a specimen with the use of plasmon resonance, said method comprising the steps of:

forming an insulating layer on a substrate, the surface of the substrate having an electroconductive layer including a first electroconductive material;

forming a plurality of holes through the insulating layer to form an insulating pattern;

filling up the holes with a second electroconductive material to form a metallic pattern;

removing the insulating pattern; and removing a region in the electroconductive layer, using the metallic pattern as a mask.

2. The method of producing a sensing element according to claim 1, wherein the first electroconductive material is comprised of silver, and the second electroconductive material is comprised of gold.

3. The method of producing a sensing element according to claim 1, wherein said filling step includes electroplating.

4. The method of producing a sensing element according to claim 1, wherein the metallic pattern is comprised of metal dots, each of the metal dots having a size ranging from 50 nm to 450 nm.

5. The method of producing a sensing element according to claim 1, wherein the holes have a size ranging from 50 nm to 450 nm.

* * * * *

UNITED STATES PATENT AND TRADEMARK OFFICE
CERTIFICATE OF CORRECTION

PATENT NO.       : 7,403,287 B2
APPLICATION NO.  : 11/448070
DATED            : July 22, 2008
INVENTOR(S)      : Miki Ogawa et al.

It is certified that error appears in the above-identified patent and that said Letters Patent is hereby corrected as shown below:

COLUMN 4:
    Line 10, "In the next place," should read -- Next, --.
    Line 65, "gives influence to" should read -- influence --.

COLUMN 5:
    Line 3, "having" should read -- it has --.
    Line 55, "general" should read -- typical --.
    Line 58, "makes" should read -- causes --.
    Line 59, "trasnmit" should read -- to transmit --.
    Line 66, "transmitted" should read -- been transmitted --.

COLUMN 6:
    Line 11, "In the next place," should read -- Next, --.
    Line 34, "bilayer" should read -- double layer --.
    Line 51, "transmitted" should read -- been transmitted --.
    Line 52, "transmitted" should read -- been transmitted --.
    Line 53, "transmitted" should read -- been transmitted --.

COLUMN 8:
    Line 13, the first occurrence of "is" should be deleted.

COLUMN 11:
    Line 61, "droxysulfoscuccinimide" should read -- droxysulfosuccinimide --.
    Line 64, "made" should read -- made by --.

COLUMN 13:
    Line 24, "toulene" should read -- toluene --.

COLUMN 14:
    Line 8, "display" should read -- displaying --.
    Line 24, "may" should read -- or may --.

UNITED STATES PATENT AND TRADEMARK OFFICE
CERTIFICATE OF CORRECTION

PATENT NO. : 7,403,287 B2
APPLICATION NO. : 11/448070
DATED : July 22, 2008
INVENTOR(S) : Miki Ogawa et al.

It is certified that error appears in the above-identified patent and that said Letters Patent is hereby corrected as shown below:

COLUMN 15:
Line 26, "N-Hy-" should read -- N-hy- --.
Line 28, "1-Ethyl-3" should read -- 1-ethyl-3 --.

COLUMN 18:
Line 7, "may" should read -- or may --.
Line 28, "to" should be deleted.

COLUMN 21:
Line 13, "may" should read -- or may --.

Signed and Sealed this

Third Day of February, 2009

JOHN DOLL
*Acting Director of the United States Patent and Trademark Office*